United States Patent [19]

Crawford

[11] Patent Number: 4,894,052
[45] Date of Patent: Jan. 16, 1990

[54] FLASH DETECTION IN AN OVER THE NEEDLE CATHETER WITH A RESTRICTED NEEDLE BORE

[75] Inventor: Mark A. Crawford, Sandy, Utah

[73] Assignee: Becton, Dickinson and Company, Franklin Lakes, N.J.

[21] Appl. No.: 234,664

[22] Filed: Aug. 22, 1988

[51] Int. Cl.$^4$ .............................................. A61M 5/18
[52] U.S. Cl. ...................................... 604/63; 604/165; 604/168
[58] Field of Search ................. 604/168, 164, 170, 53, 604/272

[56] References Cited

U.S. PATENT DOCUMENTS

| | | | |
|---|---|---|---|
| 4,317,445 | 3/1982 | Robinson | 604/168 |
| 4,655,750 | 4/1987 | Vaillancourt | 604/168 |
| 4,772,267 | 9/1988 | Brown | 604/168 |

Primary Examiner—Stephen C. Pellegrino
Attorney, Agent, or Firm—Aaron Passman

[57] ABSTRACT

A flash cavity is positioned between the inside of a translucent over the needle catheter and a needle for providing flash detection. The needle bore is connected to the cavity by an access port positioned near the location where the tip of the catheter sealably engages the needle. The needle bore is flow restricted between the access port and a hub for manipulating the needle. In one form of the introducer, a guide wire positioned by a syringe plunger carried for movement in a syringe barrel, is used to advance the catheter into the vessel. The syringe barrel restricts passage of liquid blood, but vents gases. In another arrangement of the introducer, a porous vent plug cooperates with the end of the needle and the catheter adapter to restrict blood flow through the needle bore and to prevent escape of blood while permitting escape of gases. A method of using the flash cavity for the early detection of blood provides for the proper placement in a blood vessel of the tip of the needle and catheter carried therewith wherein the needle has a restricted needle bore and a needle hub prevents escape of blood.

17 Claims, 2 Drawing Sheets

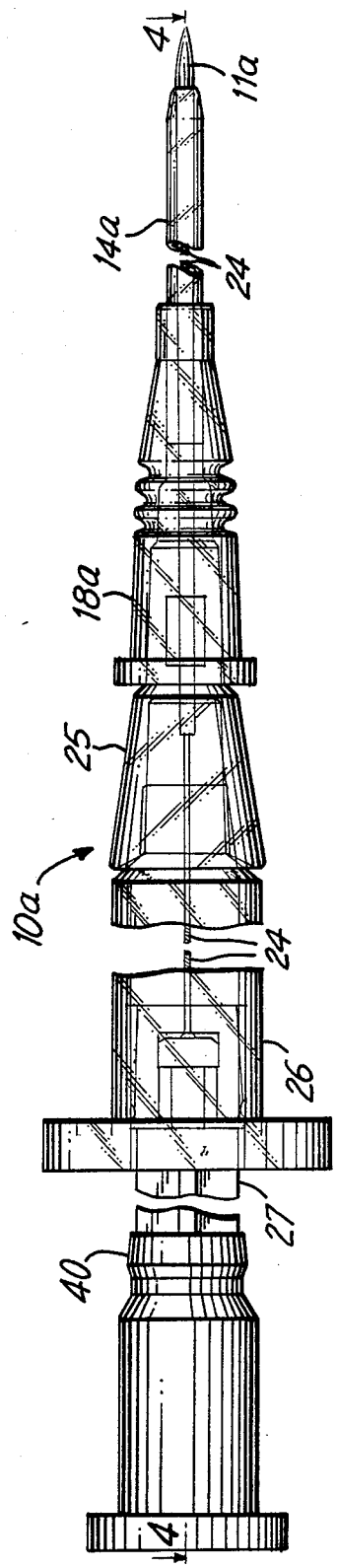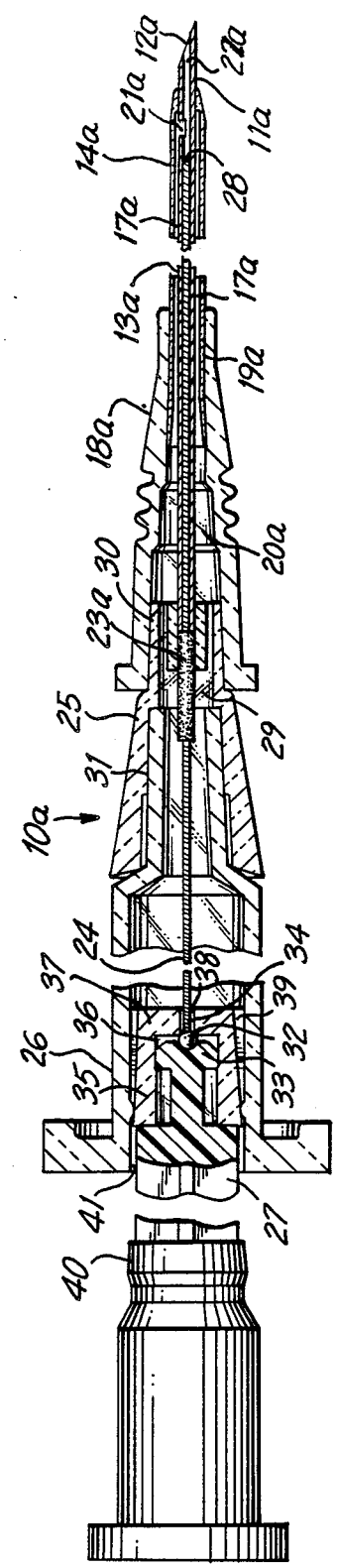
FIG. 3
FIG. 4

(4,894,052)

FLASH DETECTION IN AN OVER THE NEEDLE CATHETER WITH A RESTRICTED NEEDLE BORE

Background of the Invention:

1. Field of the Invention.

This invention relates to over the needle catheters, and more specifically, to the detection of the moment when the needle tip has pierced the blood vessel such that blood entering the needle can be observed immediately.

2. Background Description.

Observation of blood in the needle hub is called blood flash, and flash indicates the position of the needle tip. That is, when the vessel wall is penetrated by the needle bevel, flash is seen in the hub. This ordinarily takes place in a translucent needle hub flash chamber. The chamber allows the visual observation of blood from the needle. The vessel penetration by the needle tip is observable because blood flows through the bore of the hollow needle into the flash chamber when the needle is properly placed within the vessel. Similarly, needle hubs are designed to contain blood flash and vent gases and such designs also restrict blood flow through the needle bore.

The most commonly used needles each includes a bore and each needle extends from a hub so that after the needle is placed into a blood vessel, blood may be observed in the hub as an indication of successful placement. The catheter coaxially placed over the needle is carried into the vessel with the needle. Placement techniques in arterial vessels often require a guide wire for use in feeding the catheter off of the needle and into the artery after successful penetration. Guide wires restrict blood flow through the needle bore impeding the flow of blood into the hub.

Over the needle catheters, which are currently available, have a flash chamber as described. Needle bevel penetration into the vessel may not be detected immediately with current products. Delay in detection of flash results with low blood pressure, small blood supply in small vessels, small needle inner bore diameter, or a guide wire or other restriction within the needle bore. Each of those conditions impedes blood flow through the needle to the hub chamber. A flash detection delay prevents the medical technician from knowing of the precise needle bevel location under the skin. This can result in failure to penetrate the lumen of the vessel or in penetration of the vessel back wall. If the back wall is penetrated, the needle must be slowly withdrawn until flash is apparent in the hub flash chamber. If no flash is seen, the needle ad catheter must be withdrawn entirely and a new effort will have to be made to insert the needle and catheter into another vessel. Puncture of the back wall often makes the vessel unusable as a catheter site.

Skilled medical technicians are usually able to place the needle tip and coaxially carried catheter into the blood vessel without difficulty because of the experience they have in observation of flash rate. That is to say that flash will appear in a flash chamber at a speed and pressure which are related to the flow rates of the patient's cardiovascular system and the needle bore. Healthy, normal adults can give a relatively high rate of flash blood flow which is typically restricted only by the needle size. Children and people with small blood vessels and low blood pressure generally produce a relatively low rate of flash blood flow.

Several arrangements for allowing blood flow between the outside of a needle and the inside of an over the needle catheter have been proposed. U.S. Pat. No. 3,030,953 shows an over the needle catheter, which includes a needle having a short length of bore extending from the bevel to a long length groove extending axially along the shank of the needle whereby blood flash is visible once the end of the needle and the catheter tube have penetrated a vein. The catheter tube is transparent polyethylene. The rather complicated arrangement of the bore and groove requires sophisticated forming operations to create the path through the needle tip and along its shank for blood flash.

U.S. Pat. No. 3,492,992 shows a catheter and a solid needle having a longitudinal groove on the surface of the needle connecting with a circumferential groove located between the needle tip and the end of the catheter. Blood flash enters between the catheter and the needle and thereafter travels up the longitudinal groove. An alternate embodiment has an axial bore hole which turns and extends radially into an internal longitudinally extending groove up the body of the needle.

U.S. Pat. No. 3,352,306 has a solid needle with a generally cylindrical body with either a flat relief or a channel on one side. Blood flows along the flat or channel and within the catheter to the adapter during introduction of the catheter into a vessel. The blood does not pass through the needle carrying hub. Needle blood flow restrictions are dealt with by these various constructions and techniques but flow restriction due to hub design for facilitating introduction of an arterial catheter and/or for containing flash blood has not been specifically addressed.

A variety of guide wire manipulating introducers have been used to assist in feeding the over the needle catheter into a vessel. Most of these introducers include a hub with a means for moving the guide wire through the needle and for containing the flash. Similarly, flash chambers with means for separating blood from gases and capturing flash are also available. The combination of an easy to manipulate guide wire and flash chamber which permits early flash detection has not been provided.

A porous plug has been used to vent a catheter flash chamber and to carry a wire stylet as shown in U.S. Pat. No. 4,193,399. A porous plug has not been used to carry a needle, to vent an adapter and to manipulate the needle.

A catheterization method and device, which permits blood flow about a needle and into a hub for containing the blood flash and venting gases, has not been disclosed.

SUMMARY OF THE INVENTION

The catheter introducer of the present invention carries a coaxially placed over the needle catheter into a blood vessel. A needle with an inside surface and an outside surface and a bore includes a tip at one end and a hub at the other. A catheter with a thin translucent wall formed for coaxial placement over the needle which carries the catheter when penetrating a blood vessel. The distal end of the catheter terminates near the needle tip and the catheter extends proximally therefrom along the needle almost to the hub. A catheter adapter connects in fluid tight relation to the catheter proximal end. An internal chamber within the adapter is shaped to fit over the needle hub.

A cavity between the needle outside surface and the catheter extends along the needle from the distal end of the catheter to the hub. A port passing through the needle from its bore to the cavity permits blood flow from the needle tip through the cavity and into the adapter. A restriction associated with the hub and within the needle inhibits flow through the needle. Means in the hub cooperate with the internal chamber of the catheter adapter permitting fluid from the cavity to pass into the hub where liquid blood is contained and gases are vented.

The cavity may be annular extending from a relatively tight seal or interference fit between the distal end of the catheter and the outside surface of the needle.

A port provided through the wall of the needle is preferably located within the catheter adjacent the seal. Blood from the penetrated vessel, enters the hollow needle bore, flows into the needle, through the port and fills an annular cavity. A translucent catheter material allows rapid observation of blood flash between the body of the needle and the catheter. In the preferred embodiment, the port and needle bevel are open outwardly in a direction normal to the bore.

A guide wire in the needle inhibits blood flow in the needle bore. In the preferred form of the invention, blood passes through the bore to the port and the cavity before the blood reaches the guide wire. The hub may include passages to permit blood flow from the cavity to a blood collection and gas venting means.

In use, the needle tip is caused to penetrate the skin of the patient at a slight angle and enter the blood vessel with the tip directed generally parallel, but at a slight angle to the center of the blood vessel. After vessel penetration, blood enters the bore of the needle and passes through the port and fills the cavity. Since the port is proximal to where the catheter is sealed, the blood progresses from the sealed end along the needle into the catheter adapter chamber. Means in the needle hub allow blood to be contained and gases to be vented.

In another form of the introducer, blood in the cavity passes into the catheter adapter chamber. The chamber is shaped to be closed by a hub in the form of a porous plug which may be molded of a liquid impermeable gas permeable polymer so as to vent gas but retain liquid blood. The porous plug carries the needle such that once successful penetration of the vessel has been made, the plug and needle can be removed from the catheter and adapter. The porous plug restricts blood flow through the needle bore causing the blood to pass into the cavity between the needle and catheter.

This invention includes a method for rapid detection of flash during insertion of a translucent or transparent over the needle catheter with a flash detection cavity between the inside of the catheter and the outside of an elongate needle. The needle ha a bore therethrough and a port extending radially between the bore and the cavity which extends into a catheter adapter having an opening connected to the catheter at one end and closed by a needle hub at the other end, so that the hub receives and contains blood and vents gases from the adapter.

The inventive method steps include orienting the needle bevel to face from the patient s skin and in alignment with a blood vessel. The needle axis is at a slight angle to the skin for insertion into the blood vessel before penetrating the vessel. The needle bore is restricted in the area proximal of the port inhibiting blood flow. The needle tip is inserted into the patient's blood vessel and urged inwardly until blood flow is observed in the cavity between the inside wall of the catheter and the outside wall of the needle. The needle hub is manipulated to remove the needle from the catheter.

The device, of this disclosure is useful for people with relatively low blood pressure, or small blood vessels; it permits observation of flash in the catheter carried over a needle having a restricted bore which does or will not allow free flow of blood.

BRIEF DESCRIPTION OF THE DRAWINGS

FIG. 3 is a top plan view of a preferred embodiment of a needle and over the needle catheter introducer wherein a syringe and guide wire are included as part of the hub.

FIG. 4 is a longitudinal cross sectional view taken along line 3—3 of FIG. 3 showing the relationship of the guide wire terminating within the hollow needle proximal of the access port and the syringe for containing liquid blood and venting gases.

DETAILED DESCRIPTION OF THE DRAWING

Figure 1:
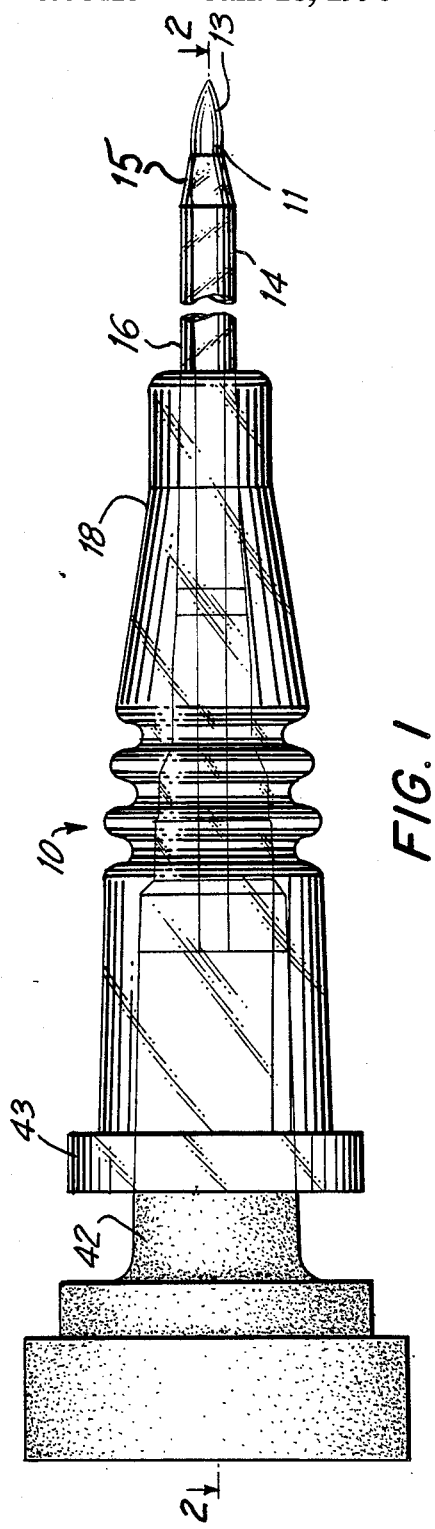
FIG. 1 is a top plan view of an embodiment of a needle and an over the needle catheter introducer with a needle hub of a porous liquid impermeable and gas permeable material.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

In FIG. 1, there is an introducer 10 for an over the needle catheter including an elongate tubular hollow needle 11 having a beveled tip 12. The bevel is angled at an angle "A" relative to an outside of wall 13 of the elongate tubular hollow needle 11. A catheter 14, preferably extruded of translucent or transparent polymeric material such as polyurethane, is positioned coaxially over the needle 11. Catheter 14 has a relatively thin wall section with a tapered distal end 15. The construction of the preferred catheter 14 may be found in U.S. Pat. 4,588,398 which is included by reference as a part of this disclosure. The catheter material and the sealed or interference fit of catheter end 15 with the outside wall of the needle are also explained in U.S. Pat. 4,588,398.

The interference fit of catheter end 15 with the outer diameter of the elongate tubular hollow needle wall 13 circumscribes and holds end 15 against the outside of wall 13 of the needle 11 to form a seal. Clearance between the remaining body 16 of the catheter 14 and the outside of wall 13 of the needle 11 creates an annular cavity 17 which extends axially upwardly from the seal between the catheter end 15 and the outside of wall 13 along the needle 11 to a catheter adapter 18. Catheter adapter 18 attaches to the catheter 14 with a fluid tight connection at the proximal end 19 of the catheter 14, see FIG. 2. The adapter 18 includes a chamber 20 shaped to receive a luer fitting such that medication may be infused or blood samples may be taken.

Figure 2:
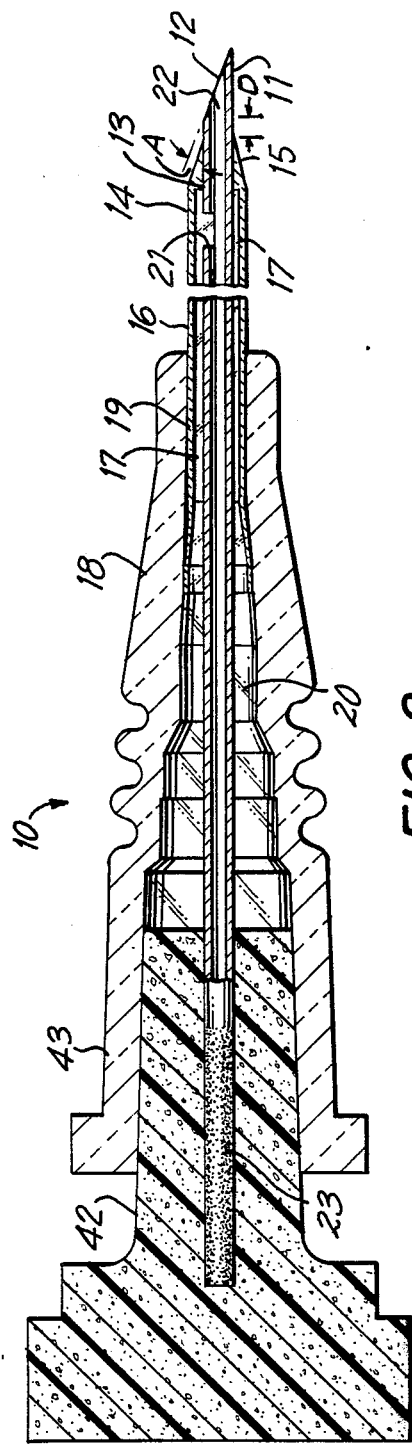
FIG. 2 is an enlarged longitudinal cross sectional view taken along line 2—2 of FIG. 1 wherein the relationship of an access port and an annular cavity between the catheter and an outer wall of the needle are shown in combination with the porous plug hub.

In FIG. 2, an access port 21 forms a passage between the annular cavity 17 and a hollow inside bore 22 of the needle 11. Access port 21 may be cut or notched into the wall of the needle 11 at a point proximal the area of the seal between the catheter end 15 and outside wall 13 of the needle 11. Access port 21 permits blood flow between annular cavity 17 and the hollow inside bore 22 which extends to needle tip 12 in one direction and to a proximal end 23 of needle 11 in the other direction. Flowing blood, through the needle hollow bore 22, fills the needle bore 22 up to the access port 21. The blood may then pass through the access port 21 and fill the annular cavity 17 between the catheter body 16 and the outside of wall 13 of the needle 11. Because of the preferred metallic finish of the outside of wall 13 of needle 11, the translucent nature of catheter material and the catheter seal between the catheter end 15 and the outside of wall 13 of the needle 11, blood rising upwardly in annular cavity 17 may be readily observed over the outside of wall 13 of the needle 11.

In use, the medical technician may make the described needle penetration. The needle 11 coaxially carries with it the catheter 14 whereby the catheter tapered end 15 enters the vessel. The distance designated "D" in FIG. 2, between the end 15 of the catheter 14 and the heel or proximal edge of the bevelled tip 12 of the needle 11, is referred to as, "the lie distance" and is typically 0.254 mm. or 0.010 inches. Distance "D" is precisely set by the axial placement of the catheter 14 due to the configuration of the adapter 18 which fits over the hub. Consequently, placement of the needle 11 into the vessel also positions the catheter end 15 inside the blood vessel. Once flash is observed, the catheter 14 is simultaneously advanced or threaded into the vessel while the needle is withdrawn. Experienced medical technicians develop a feel for this procedure.

FIG. 1 and 2 have like parts labeled with the similar reference numerals. For example, catheter 14 is coaxially positioned over the needle 11 with the catheter tip 15 forming a tight seal about the needle 11. In FIGS. 3 and 4 the suffix "a"is used with the reference numerals used on the parts shown FIGS. 1 and 2 even these are different embodiments of the invention.

In arteries, the advancement of the catheter is difficult because the arterial blood vessel wall resists the movement of the relatively soft and flexible catheter through the wall. An embodiment for introducing catheters into arteries is shown in FIG. 3 and 4 that introducer 10a has a guide wire 24 to stiffen a catheter 14a during advancement into the vessel. The guide wire 24 fits within the elongate tubular hollow needle bore 22a for reciprocatory movement. Needle 11a is supported by a needle hub 25 at its proximal end 23a for manipulation. In this preferred embodiment of FIG. 3, blood is collected in the hub 25 and a syringe barrel 26 with a syringe plunger 27. Guide wire 24 extends proximally beyond the proximal end 23a of the needle 11a into the syringe barrel 26. The guide wire 24 carried upon and extending from syringe plunger 27 aligns with the needle bore 22a, see Figure 4. The guide wire 24 may be connected by any one of several suitable methods to the plunger 27. The guide wire 24 extends from plunger 27 with sufficient length extending therefrom to allow the guide wire 24 and the syringe plunger 27 when fully retracted relative to syringe barrel 24 to position a far end 28 of the guide wire 15 near access port 21a, as shown in Figure 4.

In the preferred method of use for the preferred embodiment of the arterial introducer 10a in FIGS. 3 and 4, the medical technician makes the needle penetration with the syringe plunger 27 and guide wire 24 fully retracted. At the time of the vessel penetration by the bevelled needle tip 12a, blood fills the needle bore 22a to the far end 28 of the guide wire 24. When the blood reaches access port 21a, it passes through access port 21a and begins filling the annular cavity 17a. Blood flowing toward the hub end 23a of the needle 11a is restricted from flowing through the bore 22a by the location of guide wire 24. Because the guide wire 24 is positioned proximally within the needle bore 22a to access port 21a, the restricted needle bore 22a inhibits or prevents the flow of blood to the proximal end 23a of the needle 11a. The hub 25 includes several longitudinal passages 29 which extend from the catheter adapter 18a to the syringe barrel 26. Specifically, the adapter 18a includes an internal chamber 20a which receives a tapered male luer 30 on the hub 25. A fluid tight coupling relationship is formed between the tapered luer 30 and the inside of chamber 20a. Syringe barrel 26 also has a luer slip 31 on its distal end, and luer slip 31 fits into hub 25 to form a fluid tight connection. The instantaneous blood flash will be apparent in the annular cavity 17a, as observed through the translucent catheter 14a, long before any blood would reach the syringe barrel 26.

In FIG. 4, the syringe plunger 27 is shown in its withdrawn or retracted position and the guide wire 24 extends from a ball socket 32 centered in the distal end 33 of the plunger 27. In particular, the proximal end 34 of guide wire 24 has a ball shape dimensioned to fit within socket 32. A cap 35 is cup shaped with a hollow interior 36 for fitting over the distal end 33 of plunger 27 and for holding the ball shaped end 34 in socket 32. In the bottom 37 of cap 35 a centrally located bore 38 permits guide wire 24 to extend outwardly and through the needle bore 22a.

The cap 35 has a plurality of ribs 39 longitudinally disposed about the outside of the cap 35. The longitudinal ribs 39 are positioned to support and center the cap 35 during reciprocatory movement with the plunger 27 within the syringe barrel 26. Each rib 39 extends radially from the cap 35 leaving spaces between adjacent ribs 39 which spaces permit blood and gases within the barrel 26 to move past the plunger cap 35, when the plunger 27 is moved axially through the barrel 26 while the barrel 26 has blood within it.

The guide wire 24 and plunger 27 operate to aid in introducing a catheter 14a into a vessel. The needle 11a and catheter 14a are inserted into the vessel as explained. When flash is seen within the annular cavity 17a , the medical technician slowly depresses the syringe plunger 27 to advance guide wire 24 through the needle bore 22a until it enters the vessel. Advancement of the guide wire 24 continues until its far end 28 is properly positioned with the vessel.

The plunger 27 includes a stopper 40 at its proximal or user end. Stopper 40 seats inside syringe barrel 26 when the plunger 27 and guide wire 24 have been fully advanced. Advancement of the guide wire 24 closes access port 21a preventing flash from continuing to flow through the cavity 17a. The syringe barrel 26 is sealed at its proximal end 41 by the stopper 40 preventing any blood which had previously passed through the spaces between the ribs 39, and was already within the syringe barrel 26, from escaping. The catheter 14a may then be advanced off the needle 11a, over the guide wire 24 and into the vessel. During advancement of the catheter 14a the guide wire 24 acts to stiffen the normally flexible catheter 14a. After the catheter 14a is positioned within the vessel, the needle 11a, guide wire 24 and syringe barrel 26 are withdrawn as an assembly from the placed catheter 14a. The assembly does not leak because the guide wire 24 occludes the needle 11a and the stopper 40 seals the syringe barrel 26. The catheter 14a does not leak because the medical technician presses against the catheter 14a near the puncture site to stop blood flow through the catheter 14a until the adapter 20a can be connected to an appropriate medical device. Contaminated flash blood is contained within the introducer syringe 10a.

Blood flow rates of patients vary considerably in accordance with the nature of the vessel used for the catheterization and the particular location of the vessel relative to the patient's heart. It has been found that for pediatric patients and others with low blood pressure and small blood vessels, the early detection of flash in the annular cavity 17 or 17a is useful for placement of the needle tip 12 or 12a during an insertion of an over the needle catheter 14 or 14a. Early detection of the exact position of the needle 11 or 11a will help even skilled medical technicians to know the location of the needle tip 12 or 12a relative to the vessel during placement of the needle 11 or 11a. It is particularly difficult to anticipate the exact position and size of the blood vessel as every patient is different. The blood vessel location, shape and depth (amount of skin between the vessel and the surface) is unique to each individual patient. The size of the access port 21 or 21a may be changed, i.e. smaller in order to restrict flow and change the rate of blood passing from the hollow inside bore 22 or 22a of the needle 11 or 11a whereby the device would be useful for adult patients having normal or even high blood flow rates. Similarly, the annular cavity 17 or 17a may be increased or decreased in cross sectional area such that flow rates will be enhanced or diminished as required. The exact size of annular cavity 17 or 17a is determined as a function of the particular needle and catheter gauge and wall thickness. In addition, the needle bevel 12 or 12a and access port 21 or 21a are both open in the same direction normal to the elongate needle and this places the access port 17 or 17a upwardly relative to the bottom inside of the vessel.

It should be appreciated that the present invention gives an earlier determination of the location of the needle tip 12 or 12a by immediate blood flash detection in annular cavity 17 or 17a between the outer wall 13 or 13a of the needle 11 or 11a and the catheter 14 or 14a. The need to vent gases and contain blood may be satisfied by means other than a syringe barrel 26 as a hub fit to the luer end 30 of an adapter 18a.

In a catheter insertion procedure without a guide wire, wherein the catheter adapter 18 fits about a needle hub having a flash chamber, the present invention has value. FIGS. 1 and 2 show a hub 42 for the needle 11, which is a porous vent plug. Porous vent plug hub 42 may be formed of a polymer so as to permit the flow of gases while restricting the passage of liquid blood. Plug hub 42 is preferably shaped to fill the space between the proximal end 23 of the needle 11 and the luer end 43 of the adapter 18. In FIG. 2, the proximal end 23 of the needle 11 is shown full and not in section. A rough surface finish is applied to the needle proximal end 23 (as for example, sand blasted or etched) where the needle 11 is held in the porous plug hub 42. As with the introducer 10a for a catheter 14a of FIGS. 3 and 4, the device of FIGS. 1 and 2 restricts the flow of blood through its needle bore 22. Specifically, the porous plug hub 42 closes the proximal end 23 of needle 11 and that coupled with the small diameter of the needle bore 22 greatly inhibits flow through the needle bore 22. Blood flowing up the needle hollow bore 22, through the cavity 17 and within the adapter 18 does not pass through the porous vent plug hub 42, only gases pass through the porous plug hub 42. The preferred plug hub 42 is a hydrophobic sintered polyolefin material, which is gas permeable and liquid impermeable.

In use, blood flash immediately appears between the catheter 14 and the outside needle wall 13 of the needle 11 as that is the least restrictive path for the blood flowing through the bore 22. Blood filling annular cavity 17 eventually reaches the interior chamber 20 of adapter 18 and fills that as well. The porous vent plug hub 42 permits gases to be vented from the proximal end 23 of the needle and from the inside chamber 20 of the adapter 18, but will not allow blood to escape. A hub which combines the vent plug and end closure functions for the adapter 18 is a simple device for manipulating the needle 11 and provides an improvement by eliminating extra components which have to be disposed after use.

Blood contamination is a serious health hazard and the introducer of FIGS. 1 and 2 minimizes the disposal problem by containing the blood in the adapter with a simple hub 42. After removal of the needle 11 and hub 42 from the catheter 14, application of pressure to the inserted catheter 14 near the puncture site stops blood flow. After the hub 42 and needle 11 have been discarded the pressure applied to the site of the puncture of the catheter 14 permits an essentially bloodless connection procedure for the adapter 18 and the administration line.

The introducers 10 and 10a described in connection with FIGS. 1, 2, 3 and 4 have solved the problem of providing a path for flash between the catheter and flash chamber where the needle bore 22 or 22a is restricted preventing blood flow through the needle bore. Those skilled in the art will appreciate that changes in the material of the catheter, the size, shape and precise position of the access port, the restriction of the needle bore, the way of sealing the catheter tip to the outer wall of the needle or how the introducer is used may be made without departing from the scope of the invention covered by the claims which follow.

WHAT IS CLAIMED:

1. A catheter introducer for carrying a coaxially placed over the needle catheter into a blood vessel comprising:
   a needle assembly including an elongate hollow tube including a wall defined by an inside and an outside surface with a bore therethrough and a tip at one end of said tube and a hub at the other;
   a tubular translucent catheter formed for coaxial placement over said needle tube and to be carried thereby during a penetration procedure for introducing said catheter into a blood vessel and said catheter being elongate with an end positioned just proximal to said needle tip and extending therefrom over and along said tube toward said hub;

a catheter adapter having a body connecting to said catheter at an end near said needle hub and fitted to said catheter in fluid tight relation, and said body including an internal chamber shaped to fit over at least a part of said hub coaxially aligning said catheter relative to said needle tube;

a cavity located between said outside surface of said tube, said catheter extending along said needle tube from said catheter tip end to said hub end;

a port passing through said needle tube from said bore to said cavity for permitting fluid communication from said needle bore near said needle tip to said cavity near said hub;

restriction means associated with said hub for substantially inhibiting flow through said bore within an area in said bore between said port and said hub; and blood separation and venting means associated with said hub for cooperating with said catheter adapter chamber to allow liquid in said cavity to remain in a portion of said hub which contains liquid blood and vents gas.

2. The catheter introducer of claim 1 wherein said cavity is an annular elongate space between said outside surface of said needle and the inside of said tubular catheter, which space extends from where said catheter adapter is fitted to said catheter to a position on said needle tube distal to said port.

3. The catheter introducer of claim 2 wherein said needle end of said catheter is an interference fit relative to said needle outside surface for forming a sealed connection.

4. The catheter introducer of claim 1 wherein said restriction means associated with said hub and said needle bore resists blood flow through said bore greater than blood flow through said port and said cavity.

5. The catheter introducer of claim 1 wherein said blood separation and venting means includes a syringe barrel having a plunger therein for reciprocal movement of said plunger within said hub.

6. The catheter introducer of claim 1 wherein said blood separation and venting means includes a plug formed of a porous gas permeable and liquid impermeable material, said plug being configured to extend over said needle bore and occupy an area between said adapter and said needle assembly hub for preventing liquid flow from said adapter chamber while permitting gases to pass outwardly through said plug.

7. An early flash detection arrangement for an arterial introducer apparatus having a guide wire to assist in the insertion of an over the needle catheter assembly comprising:

an elongate tubular hollow needle assembly including a bore therethrough, a beveled tip at one end of said needle assembly, a hub at the other end and therebetween a uniformly shaped body having an outside surface;

a thin translucent polymeric catheter tube with a taper at one end and an adapter at the other end, so that said catheter tube, when placed coaxially over said needle assembly body with said taper sealably engaged about said needle body outside surface proximal said beveled needle tip, locates said adapter to coaxial engage and fit over at least a distal part of said hub;

an annular cavity between the inside of said catheter tube and said outside surface of said tubular hollow needle assembly body for extending to where said catheter taper sealably engages said needle assembly body to said hub;

an access port passing radially through said elongate tubular hollow needle assembly body from said bore to said outside surface and located proximal to where said catheter taper sealably engages said needle for forming a passageway connecting between said bore and said annular cavity;

a flash chamber in the form of a syringe barrel as a proximal part of said hub which extends from where said adapter fits over said distal part of said hub;

a plunger carried within said syringe barrel for reciprocal movement of said plunger therewithin to and from said distal part of said hub, said plunger including a distal end shaped to coaxially fit within said syringe barrel and a proximal end extending beyond said syringe barrel during manipulation;

a passage extending through said distal part of said hub providing fluid communication between said annular cavity and said syringe barrel; and a guide wire extending from said distal end of said plunger into said needle bore and mounted for movement through said needle bore in response to plunger motion in said barrel.

8. The introducer apparatus of claim 7 wherein said guide wire reaches to the hub side of said access port when said plunger is fully retracted relative to, but remaining within, said syringe barrel.

9. The introducer apparatus of claim 8 wherein said guide wire is of a length adequate to extend beyond said beveled needle tip and to close said port as said plunger is fully inserted into said syringe barrel while said catheter adapter is coaxially engaged about said hub.

10. The introducer apparatus of claim 9 wherein said plunger includes a stopper associated with said proximal end for closing said syringe barrel when said plunger is fully moved into said barrel.

11. An early flash detection arrangement for a catheter introducer assembly, comprising;

an elongate tubular hollow needle assembly having a bore therethrough;

a beveled tip at one end of said needle assembly;

a hub at the other end of said needle assembly formed of a porous gas permeable and liquid impermeable material, said hub closing said bore of said other end of said needle for restricting flow through at least a portion of said bore;

a polymeric translucent catheter tube with an inside surface, said tube at one end being shaped to sealaby engage an outside surface of said tubular hollow needle assembly proximal to said beveled needle tip for helping in the introduction of said catheter tube in an over the needle technique used to penetrate and carry said catheter into a blood vessel;

an annular cavity catheter tube and said outside surface of said tubular hollow needle assembly for extending from where the outside of said catheter sealably engages said needle assembly to an adapter;

an adapter attached in fluid tight relation to said catheter at an end opposite said one end and having a body with a chamber therein, said adapter being disposed for placement coaxially about said needle assembly, said hub and adapter each being configured to close an area between said adapter and said needle assembly to prevent liquid flow from said annular cavity and within said adapter from escaping while allowing gases to pass from said area; and an access port axially positioned through said elongate tubular hollow needle assembly an connecting between said bore and said cavity for forming a passageway to said cavity from said bore.

12. The flash arrangement of claim 11 wherein said adapter includes a female luer taper at its proximal end and said hub which coaxially carries said needle assembly is shaped for a press engagement with said luer taper of said adapter when said needle assembly is inserted through said catheter so that said beveled tip end extends beyond said catheter tube end.

13. The flash arrangement of claim 12 wherein said beveled tip is open in a direction generally normal to the elongate extent of said needle assembly and said access port is also open in said direction normal to said needle assembly elongate extent.

14. A method for inserting an over the needle catheter having an adapter at its proximal end and a flash cavity located between the inside of the catheter and the outside of an elongate hollow tubular needle carried coaxially therewithin by a hub and including an access port between the bore of the needle and the cavity and a restriction in the needle bore proximal of the port, the method including the following steps:

orienting the needle bevel so it faces away from the patient's skin and is at angle to the skin for insertion into a blood vessel;

inserting the needle tip into the patient's blood vessel and urging the needle inwardly until blood flow is observed between the catheter and the needle for indicating when the needle tip is fully inside the vessel;

observing the flash of blood between the catheter and the needle pass through the adapter to the hub;

containing flash blood within the adapter while venting gases through the hub;

removing the needle from the catheter while advancing the catheter into the vessel, and connecting the catheter by its adapter to a medical accessory.

15. The method of claim 14 including the additional step of restricting a bore through the needle and closing the port with a guide wire which passes through the needle further into the vessel after inserting the needle and over the needle catheter and before removing the needle so the catheter can be advanced over the guide wire into the vessel.

16. The method of claim 15 including the additional step of using a syringe barrel and plunger for controlling the further passage of the guide wire into the vessel when the guide wire is connected to the syringe end of a plunger.

17. The method of claim 14 including the additional step of venting the hub away from the needle end of the hub with a porous vent plug.

* * * * *